United States Patent [19]

Megyeri et al.

[11] Patent Number: 4,753,949
[45] Date of Patent: Jun. 28, 1988

[54] 2-CHLORONICERGOLINE HAVING ANTIHYPOXIC ACTIVITY

[75] Inventors: Gábor Megyeri; Tibor Keve; Bála Stefkó; Erik Bogsch; János Galambos; Anna Kassi née Zieger; Ferenc Trischler; Eva Palosi; Dóra Groo; Egon Kárpáti; Zsolt Szombathelyi; László Szporny, all of Budapest; Béla Kiss, Vecsés; István Laszlovszky; Erzsébet Lapis, both of Budapest, all of Hungary

[73] Assignee: Richter Gedeon Vegyeszeti Gyar Rt., Budapest, Hungary

[21] Appl. No.: 877,294

[22] Filed: Jun. 23, 1986

[30] Foreign Application Priority Data

Jun. 21, 1985 [HU] Hungary ............... 2447/85

[51] Int. Cl.$^4$ .................... A61K 31/48; C07D 457/02
[52] U.S. Cl. .................... 514/288; 546/67; 546/68
[58] Field of Search .................... 546/67, 68; 514/288

[56] References Cited

U.S. PATENT DOCUMENTS

| 3,228,943 | 1/1966 | Bernardi et al. | 546/68 |
| 3,879,554 | 4/1975 | Temperilli | 546/69 |
| 4,199,579 | 4/1980 | Ferrasi et al. | 546/67 |

FOREIGN PATENT DOCUMENTS

| 2700276 | 8/1977 | Fed. Rep. of Germany | 546/67 |
| 2752533 | 6/1978 | Fed. Rep. of Germany | 546/67 |

OTHER PUBLICATIONS

Bernardi et al., Ergoline Derivatives II. FARMACo. Ed. Sci. (1975) pp. 789-801.
Temperilli, CA-14782n (vol. 76) 1972.
Bernardi et al., CA, vol. 61, 3160g.
Bernardi et al., CA, vol. 80, 96201s (1974).
Hempel et al., CA 105-227104x.
Bernardi et al., CA 84-44500b.

Primary Examiner—Donald G. Daus
Assistant Examiner—Cecilia Shen
Attorney, Agent, or Firm—Jonathan Myers; Karl F. Ross; Herbert Dubno

[57] ABSTRACT

The invention relates to a novel process for the preparation of partially new 2-halonicergoline derivatives of the formula (I),

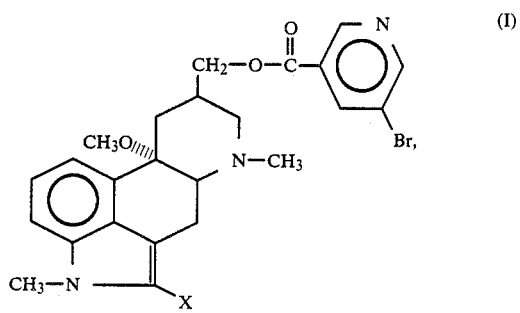

wherein
X stands for chlorine, bromine or iodine atom, as well as their acid addition salts.

The process of the invention comprises esterifying a novel 2-halo-1-methyllumilysergol of the formula (II),

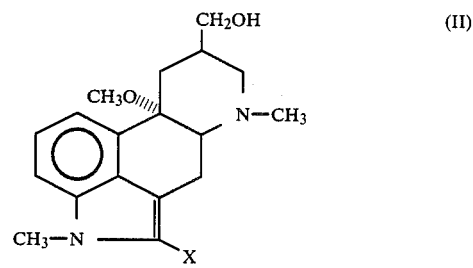

wherein X is the same as defined above, or an acid addition salt thereof and, if desired, converting the thus-obtained 2-halonicergoline derivative of the formula (I) to an acid addition salt.

The compounds of the invention improve the cognitive function of the brain and show an antihypoxic as well as a strong α-adrenerg blocking and calcium-antagonistic action.

3 Claims, No Drawings

2-CHLORONICERGOLINE HAVING ANTIHYPOXIC ACTIVITY

The invention relates to a novel process for the preparation of partially new 2-halonicergoline (1,6-dimethyl-2-halo-10α-methoxyergoline-8β-methanol 5-bromonicotinate ester) derivatives of the formula (I)

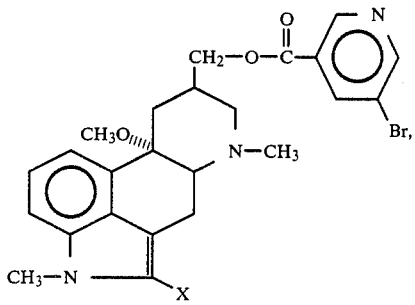

wherein
X stands for chlorine, bromine or iodine atom, as well as their acid addition salts.

According to the invention the compounds of the formula (I) and their acid addition salts are prepared by esterifying a novel 2-halo-1-methyllumilysergol (1,6-dimethyl-2-halo-10α-methoxyergoline-8β-methanol) of the formula (II)

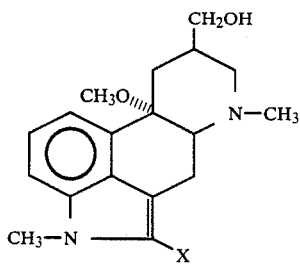

wherein X is the same as defined above, or an acid addition salt thereof and, if desired, converting the thus-obtained 2-halonicergoline derivative of the formula (I) to an acid addition salt.

Among the 2-halonicergoline derivatives of the formula (I) prepared by using the process of the invention, those compounds, wherein X stands for chlorine or iodine atom, are novel. These compounds are therapeutically active; thus, the invention also relates to the preparation of the pharmaceutical compositions containing these compounds or the acid addition salts thereof as active ingredient.

Nicergoline (1,6-dimethyl-10α-methoxyergoline-8β-methanol 5-bromonicotinate) is a known peripheral vasodilatory agent first described in the U.S. Pat. No. 3,228,943 and in the German Pat. No. 2 112 273.

Hitherto, the 2-bromo derivative of the nicergoline has only been described [L. Bernardi et al.: Il Farmaco, Ed. Sc. 30, 789 (1975)]; it possesses also a vasodilatory and α-adrenerg blocking effect. According to this paper, 2-bromonicergoline is prepared by esterifying with 5-bromonicotinoyl chloride in the presence of pyridine and the thus-obtained nicergoline is brominated in acetic acid to give 2-bromonicergoline.

It has been found in the course of our investigations that the novel compounds of the formula (I), wherein X represents a chlorine or iodine atom, possess a valuable therapeutical activity: in particular, these compounds improve the cognitive function of the brain and show an antihypoxic as well as a strong α-adrenerg blocking and calcium-antagonistic action.

The beneficial antihypoxic and cognitive function-improving effects were proved by pharmacological investigations using the following methods.

The studies were carried out on male SHR rats weighing 160 to 180 g as well as on CFLP mice of both sexes weighing 18 to 21 g. The compounds to be tested were orally administered in a volume of 5 ml/kg of body-weight (in the case of rats) or in a volume of 10 ml/kg of body-weight (in case of mice) at the 60th minute before beginning the experiment.

Nicergoline was dissolved in a tartaric acid solution of 0.4%, whereas the compounds to be tested were dissolved in a TWEEN 80 solution of 5% and diluted to the desired concentration by adding physiological saline.

The results are expressed as percentages.

Investigation of the antihypoxic effect

[I. Baumel et al.: Proc. Soc. Exp. Ther. Biol. N.Y. 132, 629 (1969]

Rats (n=5) were treated with various doses of the compounds to be tested and after 60 minutes the survival time was measured under hypobaric hypoxic conditions (170 mmHg). In the Table, the survival time is expressed as the percentage of that of the control group.

Investigation of the learning-facilitating effect

[W. B. Essmann and H. Alpern: Psychol. Rep. 41, 731 (1964)]

Mice (n=10) were treated with 5 mg/kg doses of the compounds to be tested, then the animals were conditioned by the one-trial passive avoidance method. The animals were placed on the platform of the test box, whereupon after entering into the dark box, they received an electric footshock (1.5 mA, 0.3 sec). One week later, the animals were retested: the mean of the latency period of the entering (avoidance) was compared to the control value and expressed as the percentage thereof.

Antagonism of the acquisition-inhibitory effect of hypoxia

Rats (n=4) were daily treated with various doses of the compounds to be tested, then conditioned in an automatic six-channel shuttle box (VKI) for 3 days [with the following parameters: 50 cycles/day, 15 seconds intersignal period, 15 seconds light stimulus, 10 seconds light and electric footshock (0.8 mA)] under normobaric hypoxic conditions (6% $O_2$). The values of the conditioned avoidance responses on the third day were expressed as the percentage of the deviation from the control value (CAR Δ%).

Nicergoline was used as reference drug in these experiments. The results are summarized in Table 1.

TABLE 1

| Compound | Dose mg/kg p.o. | Antihypoxic effect survival time as % of the control[1] | Facilitation of learning avoidance latency period as % of the control[2] | Antagonism of the acquisition-inhibitory effect of hypoxia[3] CAR Δ % |
|---|---|---|---|---|
| 2-Chloro-nicergoline | 1.0 | 155 | | |
| | 2.5 | 276 | | 150 |
| | 5.0 | | 182 | |
| Nicergoline | 1.0 | 103 | | |
| | 2.5 | 109 | | |
| | 5.0 | | 131 | |
| | 10.0 | | | 150 |

Notes to the Table 1:

[1] Mean survival time of control animals ($\bar{x}$ + SE) 3.3 ± 0.19 min

[2] Mean control latency period ($\bar{x}$ ± SE)
164.0 ± 34.4 sec (nicergoline)
77.0 ± 16.4 sec (2-chloronicergoline)

[3] CAR of animals conditioned among normoxic conditions: 92.0 ± 1.2%;
CAR of the animals conditioned among hypoxic conditions: 22.0 ± 5.0%.

It is obvious from the data of Table 1 that the mean survival time of the animals is not influenced by a 2.5 mg/kg dose of nicergoline under lethal hypobaric hypoxic conditions, whereas the hypoxic tolerance is significantly increased by an 1.0 mg/kg dose of 2-chloronicergoline. The deteriorated performance of the animals conditioned under normobaric hypoxic circumstances is normalized by a 4 times lower dose of 2-chloronicergoline than by that of nicergoline. On administration of the same doses, the learning-facilitating effect of 2-chloronicergoline is significantly better than that of nicergoline.

Within the biochemical investigations, the $\alpha_1$- and $\alpha_2$-adrenergic receptor and D-2 receptor binding and the synaptosomal uptake of the compounds of the invention were studied.

Investigation of the $\alpha_1$-adrenergic receptor binding

Hannover Wistar rats were decapitated, their cortex were prepared and homogenized in a 20-fold volume of a buffer solution (50 mmoles of TRIS HCl, at pH 8). The membrane was centrifuged at 45000 g twice for 15 minutes and then suspended in the buffer in a concentration of 30 ml/g (in a protein concentration of 1.7 to 1.8 mg/ml).

For investigating the $\alpha_1$-receptor binding, a membrane preparation, a ligand (0.5 nmole of $^3$H-prazosine) and the compound to be tested were used in a total volume of 1 ml. After an incubation at 23° C. for 30 minutes, the samples were filtered through a Whatman GF/B filter and washed 4 times with 4 ml of buffer solution each.

For the determination of the non-specific binding, 10 $\mu$moles of phentolamine were used. Investigation of the $\alpha_2$-adrenergic receptor binding Hannover Wistar rats were decapitated, their cortexes were prepared and homogenized in a 30-fold volume of a buffer solution (50 $\mu$moles of TRIS HCl, at pH 7.4). The membrane was centrifuged at 45000 g twice for 15 minutes and then suspended in the buffer in a concentration of 50 ml/g (in a protein concentration of 0.9 to 1.0 mg/ml).

For investigating the $\alpha_2$-receptor binding, a membrane preparation, a ligand (1.0 nmole of $^3$H Rx 781094=$^3$H-1 dazoxane) and the compound to be tested were used in a total volume of 1 ml. After an incubation at 23° C. for 20 minutes, the samples were filtered through a Whatman GF/B filter and washed 4 times with 4 ml of buffer solution each.

For the determination of the non-specific binding, 10 $\mu$moles of phentolamine were used.

Investigation of the D-2 receptor binding

Hannover Wistar rats were decapitated and the striatum from their cortex was prepared. The striata were homogenized in a 10-fold volume of a cold buffer solution (50 mmoles of TRIS HCl, 120 mmoles of NaCl, 2 mmoles of KCl, 1 mmole of MgCl$_2$ and 5 mmoles of CaCl$_2$ at pH 7.4) and centrifuged at 45000 g for 15 minutes. The thus-obtained sediment was suspended in the buffer in a concentration of 100 ml/g (in a protein concentration of 0.7 to 0.8 mg/ml).

For investigating the D-2 receptor binding, a membrane preparation, a buffer, a ligand (0.5 nmole of $^3$H-spiroperidol) and the compound to be tested in a defined concentration were used in a total volume of 2 ml. After an incubation at 37° C. for 15 minutes, the samples were filtered through a Whatman GF/B filter and washed 2 times with 5 ml of buffer solution each.

For the determination of the non-specific binding, 1 $\mu$mole of (+)-butaclamol was used.

On using all the above three receptor binding methods, a scintillation cocktail was applied onto the filter paper in the cuvet and the isotopic radioactivity was measured on the next day.

Investigation of the $^{45}Ca^{2+}$ uptake into synaptosomes

The synaptosomal fraction was prepared from rat brain cortex according to the method of Wu et al. [J. Neurochem. 39, 700 (1982)], with a protein content of 20 mg/ml.

For the experiment, a buffer solution (112 mmoles of NaCl, 5 mmoles of KCl, 1.3 mmoles of MgCl$_2$, 1.2 mmoles of NaH$_2$PO$_4$, 1.2 mmoles of CaCl$_2$, 10 mmoles of glucose and 20 mmoles of TRIS adjusted to pH 7 by carbogen at 37° C.) was used. The mixture containing the buffer solution, the compound to be tested and 1 mg of synaptosomes in a total volume of 1 ml was preincubated at 37° C. for 20 minutes and then, the K+ (45 mmoles) induced $^{45}Ca^{2+}$ upward and, for control, the Na+ (45 mmoles) induced $^{45}Ca^{2+}$ uptake were measured. The reaction was stopped by adding 5 ml of a buffer solution (120 mmoles of NaCl, 5 mmoles of KCl, 5 mmoles of EGTA and 20 mmoles of TRIS, at pH 7.4). The samples were filtered through a Whatman GF/B filter and washed 2 times with 5 ml of a washing buffer solution each (132 mmoles of NaCl, 5 mmoles of KCl, 1.3 mmoles of MgCl$_2$, 1.2 mmoles of CaCl$_2$ and 20 mmoles of TRIS, at pH 7.4). The radioactivity remaining on the filter was determined in 10 ml of scintillation solution.

The results of the determinations are summarized in Table 2.

TABLE 2

|  | $IC_{50}$ | | | $\alpha_2/\alpha_2$ | $D\text{-}2/\alpha_1$ | $IC_{50}$ |
|---|---|---|---|---|---|---|
|  | $\alpha_1$ | $\alpha_2$ nmole | D-2 | Selectivity ratios nmole/nmole | | $^{45}Ca^{2+}$ μmole |
| 2-Chloro-nicergoline | 9.5 | 24.2 | 877 | 0.39 | 92.3 | 7.0 |
| Nicergoline | 5.3 | 176 | 71.4 | 0.03 | 13.5 | 26.7 |

It is obvious from the data of Table 2 that the α-adrenergic receptor activity (adrenoceptor activity) of 2-chloronicergoline and nicergoline is practically identical: the $IC_{50}$ value of both compounds is low, a fact showing the high activity of both compounds. At the same time the $\alpha_2$-adrenoceptor activity of 2-chloronicergoline is about 13 times as high as that of nicergoline. On the other hand, the D-2 receptor activity of 2-chloronicergoline is 12 times lower than that of nicergoline. This pronounced α-adrenoceptor selectivity of 2-chloronicergoline is clearly shown by the D-2/$\alpha_1$ selectivity ratio.

An other important biochemical effect of 2-chloronicergoline consists in that its activity on the inhibition of the synaptosomal $^{45}Ca^{2+}$ uptake is about 4 times as high as that of nicergoline.

Summing up the results of the pharmacological and biochemical investigations, the 2-halogenated nicergoline derivatives seem to be effective in clinical uses similar to those of nicergoline, however the effect of the halogenated derivatives is much more intense and selective. The results of the biochemical studies are in correlation with the strong antihypoxic and brain cognitive function-promoting effects proved by the pharmacological investigations.

In the course of the preparation of 2-halonicergoline derivatives of the formula (I) according to the invention, the halogen is introduced to the $C_2$ atom of the ergolene skeleton in the first step of the synthesis path.

Surprisingly, it has been recognized in the course of our investigations that a number of unexpected advantages are provided by introducing the halogen to the $C_2$ atom of the ergolene skeleton at the very beginning of the synthesis; i.e. by the preparation of a 2-halolysergol: in the subsequent part of the synthesis the reactions proceed more simply, within a shorter time, giving higher yields together with less side-products and structural isomers as compared to intermediary products containing no halogen at the $C_2$ atom of the ergolene skeleton.

The preparation of the novel 1-methyl-2-halolumilysergol used as starting substance in the process of the invention has been described in our parallelly filed Hungarian patent application No. 2446/85. According to this patent application, 2-halolysergol is converted to 2-halolumilysergol in a photochemical reaction as described in Example 1 and the latter compound is methylated as described in Examples 2 and 3 to give 1-methyl-2-halolumiylsergol.

According to the process of the present invention, a novel 1-methyl-2-halolumilysergol of the formula (II), wherein X represents a chlorine, bromine or iodine atom, or an acid addition salt thereof is esterified. This esterification is carried out in two steps. In the first step a reactive ester is prepared and the thus-obtained compound is used in the second step for esterification.

The reactive ester is prepared in such a way that N-hydroxysuccinimide is dissolved in an aprotic solvent such as tetrahydrofuran or ethyl acetate, preferably ethyl acetate and to this solution 5-bromonicotinic acid, taken in excess, as well as N,N-dicyclohexylcarbodiimide, taken in an amount equivalent to the N-hydroxysuccinimide, are added. After stirring at room temperature, the precipitate formed is filtered and the mother liquor is evaporated under reduced pressure. If desired, the reactive ester obtained as a white amorphous material is recrystallized from ethanol.

In the next step, the esterification with the reactive ester is carried out at a temperature between 20° C. and 60° C., preferably at room temperature, in an aprotic solvent such as tetrahydrofuran, in the presence of an organic base, e.g. triethylamine or pyridine, preferably in pyridine. An excess of the organic base can be used as solvent for the esterification. 1-Methyl-2-halolumilysergol is dissolved in the appropriate solvent or in a pure organic base and the reactive ester prepared as described above is added. The reaction is followed by thin layer chromatography (TLC).

After completion of the esterifying reaction, the solvent is removed under reduced pressure, the product is separated from the organic phase by extraction and after drying and evaporating under reduced pressure, the product is recrystallized from ethyl ether. The thus-obtained substance is purified, if necessary, by column chromatography.

The 2-halonicergoline derivatives of the formula (I) are isolated as bases which are purified, if desired, by recrystallization or converted, if desired, to acid addition salts by using an appropriate acid.

The recrystallization is carried out by using a protic or aprotic solvent, preferably acetone or ether.

The salts are formed by using a protic or aprotic solvent such as an aliphatic alcohol, acetone, acetonitrile, tetrahydrofuran, ether, preferably ethanol, in such a way that the obtained 2-halonicergoline derivative of the formula (I) is dissolved in a solvent mentioned above and a solution containing an equivalent amount of the appropriate acid in one of the above solvents is added at room temperature under constant stirring. The salt formation is started by cooling to 0° C. to 5° C., whereupon the precipitated salt is filtered off. Monovalent or polyvalent organic or inorganic acids such as phosphoric, acetic, methanesulphonic, camphorsulphonic, sulphuric, perchloric, maleic, tartaric acid and the like may be used for the salt formation.

The novel 2-halonicergoline derivatives of the formula (I) can be converted into pharmaceutical compositions by mixing them with the usual non-toxic, inert, solid or liquid carriers and/or auxiliary agents which are commonly used in compositions for enteral or parenteral administration. As carriers e.g. water, gelatine, lactose, starch, pectin, magnesium stearate, stearic acid and vegetable oils, such as peanut oil or olive oil or the like can be employed. The active ingredient can be formulated to the usual pharmaceutical compositions, particularly to solid forms, such as rounded or angled tablets; dragées; capsules, e.g. gelatine capsules; pills; suppositories; or the like. The amount of the solid carrier can vary between wide limits, preferably they are used in an amount between about 25 mg and 1 g. The compositions may optionally contain commonly used pharmaceutical additives, e.g. preserving agents, stabilizers, wetting agents, emulsifying agents or the like. These compositions are prepared in a known manner; for example solid compositions are prepared by sieving, mixing, granulating and pressing the ingredients. The compositions can be subjected to additional treatments like sterilization.

The pharmaceutical composition is administered to a patient in an amount containing the dose needed to achieve the desired effect. This dose depends, inter alia, on the severity of the disease, on the body-weight and sensitivity against the active ingredient of the patient as well as on the route of the administration and on the number of the daily treatments. The dose of the active ingredient to be administered in a given case can safely be defined by the physician. In general, the effective dose lies between 0.1 and 10 mg/kg of body-weight.

The invention is illustrated in detail by the aid of the following non-limiting Examples.

EXAMPLE 1

Preparation of 2-chlorolumilysergol 2.0 g (0.007 mole) of 2-chlorolysergol are dissolved in 200 ml of a 45:75 mixture of methanol and sulphuric acid. The reaction mixture is irradiated by using a TUNGSRAM HgO 250 W lamp while keeping the temperature between 25° C. and 30° C. The reaction is followed by thin layer chromatography (TLC), by using Kieselgel 60 $F_{254}$ sheet with a 80:20 mixture of chloroform and methanol as eluant. After completion of the reaction, the solution containing methanol and sulphuric acid is clarified by 0.2 g of activated carbon, filtered, poured into 300 ml of ice-water and the pH value of the mixture is adjusted to 8 by adding aqueous ammonia. The mixture is extracted 3 times with 70 ml of chloroform each, the combined organic phase is dried over anhydrous sodium sulphate, filtered and evaporated under reduced pressure. The residue is recrystallized from acetone to give the title product in a yield of 2.0 g (90%), m.p.; 227° C.

IR (KBr, $cm^{-1}$): 2910 ($OCH_3$), 780 (aromatic halogen).

$^1$H-NMR (DMSO-$d_6$+$CHCl_3$) ($\delta$, ppm): 2.50 (s; 3H; N—$CH_3$); 2.85 (s; 3H; —O—$CH_3$); 3.55 (m; 2H; —$CH_2$—OH); 7.13–7.24 (m; 3H; aromatic hydrogen).

EXAMPLE 2

Preparation of 2-chloro-1-methyllumilysergol

After adding 1.54 g of finely pulverized potassium hydroxide to 12.7 ml of dimethylsulphoxide and stirring the mixture at room temperature for 10 minutes, 2.0 g of 2-chlorolumilysergol are portionwise added while keeping the temperature of the reaction mixture between 15° C. and 20° C. After stirring for 35 minutes, while the reaction mixture is let warm to room temperature, 0.6 g of methyl iodide is added, the mixture is stirred for additional 10 minutes then poured into 400 ml of ice-water. The precipitate is filtered off, the filtrate is evaporated under reduced pressure and the residue is recrystallized from acetone to give the title product in a yield of 1.77 g (85%), m.p; 252° C.

IR (KBr, $cm^{-1}$): 2910 ($OCH_3$), 2820 (indole-methyl), 730 (aromatic halogen).

$^1$H-NMR (DMSO-$d_6$+TFA) ($\delta$, ppm): 2.50 (s; 3H; N—$CH_3$); 2.85 (s; 3H; —O—$CH_3$); 3.55 (m, 2H; —$CH_2OH$); 3,73 (s; 3H, indole—N—$CH_3$); 7.13–7.44 (m; 3H, aromatic hydrogens).

EXAMPLE 3

Preparation of 2-bromo-1-methyllumilysergol

The process described in Example 2 is followed, except that 1.0 g (0.0027 mole) of 2-bromolumilysergol is used as starting substance. The title compound is obtained in a yield of 0.78 g (75%), m.p.; 240°–242° C.

IR (KBr, $cm^{-1}$): 2910 ($OCH_3$), 2920 (indole-methyl).

$^1$H-NMR (DMSO-$d_6$) ($\delta$, ppm): 2.49 (s; 3H; $NCH_3$); 2.97 (s; 3H; $OCH_3$); 3.55 (m; 2H; $CH_2OH$); 3.75 (s; 3H; indole N—$CH_3$); 7.17–7.41 (m; 3H; aromatic hydrogens).

EXAMPLE 4

Preparation of N-hydroxysuccinimide 5-bromonicotinate reactive ester 1.77 g of N,N-dicyclohexylcarbodiimide are added to 1 g of N-hydroxysuccinimide and 5.2 g of 5-bromonicotinic acid dissolved in 100 ml of abs. ethyl acetate at 50° C. The reaction mixture is stirred at room temperature for 4 hours, then cooled to 5° C. and the precipitated white crystals are filtered off. The filtrate is evaporated under reduced pressure and the residue is recrystallized from ethanol.

EXAMPLE 5

Preparation of 2-chloronicergoline 0.96 g of the reactive ester prepared as described in Example 4 is added to a solution containing 1 g of 2-chloro-1-methyllumilysergol in 100 ml of anhydrous pyridine. The mixture is stirred at room temperature for 4 hours while the course of the reaction is followed by TLC. After completion of the esterification, the reaction mixture is evaporated under reduced pressure, the residue is poured into 200 ml of 10% sodium carbonate solution and extracted 3 times with 30 ml of chloroform each. The chloroformic phase is washed with water. The combined organic phase is dried over anhydrous magnesium sulphate, filtered, evaporated under reduced pressure and the residue is recrystallized from ether. If necessary, the thus-obtained product is purified by chromatographic treatment to give the title compound in a yield of 1.47 g (95%).

$^1$H-NMR ($CDCl_3$) ($\delta$, ppm): 2.48 (s; 3H; N—$CH_3$); 2.53 (s; 3H; O—$CH_3$); 3.74 (s; 3H; indole N—$CH_3$); 7.0–7.28 (m; 3H; aromatic hydrogens, indole); 8.45 (t; 1H; aromatic H); 8.9 (d; 1H; aromatic H); 9.2 (d; 1H; aromatic H).

EXAMPLE 6

Preparation of 2-bromonicergoline

The process described in Example 5 is followed, except that 1 g of 2-bromo-1-methyllumilysergol is used as starting substance. The title compound is obtained in a yield of 1.4 g (95%), m.p.; 142°–144° C.

What is claimed is:

1. 2-Chloronicergoline or a pharmaceutically acceptable acid addition salt thereof.

2. An antihypoxic pharmaceutical composition which comprises a therapeutically effective amount of 2-chloronicergoline or a pharmaceutically acceptable acid addition salt thereof in combination with a pharmaceutically acceptable inert carrier.

3. A method of exerting antihypoxic, α-adrenerg blocking and calcium-antagonistic action characterized by administering a therapeutically effective amount of the compound as defined in claim 1, or a pharmaceutically acceptable acid addition salt thereof.

* * * * *